United States Patent
Alig et al.

(10) Patent No.: US 6,265,430 B1
(45) Date of Patent: *Jul. 24, 2001

(54) 3-THIOCARBAMOYLPYRAZOLE DERIVATIVES AS PESTICIDES

(75) Inventors: Bernd Alig, Königswinter; Achim Bertsch, Köln; Dietmar Bielefeldt, Ratingten; Norbert Lui, Köln; Albrecht Marhold, Leverkusen; Christoph Erdelen, Leichlingen; Wolfram Andersch, Bergisch Gladbach; Andreas Turberg, Haan; Norbert Mencke, Leverkusen, all of (DE)

(73) Assignee: Bayer Aktiengesellschaft, Leverkusen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,994
(22) PCT Filed: Nov. 21, 1997
(86) PCT No.: PCT/EP97/06503
   § 371 Date: May 6, 1999
   § 102(e) Date: May 6, 1999
(87) PCT Pub. No.: WO98/24769
   PCT Pub. Date: Jun. 11, 1998

(30) Foreign Application Priority Data

Dec. 4, 1996 (DE) ............................................. 196 50 197

(51) Int. Cl.⁷ .................. A01N 43/56; C07D 231/44; C07D 403/04
(52) U.S. Cl. .................. 514/407; 514/404; 514/406; 548/364.1; 548/367.4; 548/371.7
(58) Field of Search ............... 548/364.1, 367.4, 548/371.7; 514/404, 406, 407

(56) References Cited

U.S. PATENT DOCUMENTS

| | | | |
|---|---|---|---|
| 4,804,675 | 2/1989 | Jensen-Korte et al. | 514/407 |
| 4,945,165 | 7/1990 | Jensen-Korte et al. | 548/362 |
| 4,963,575 | 10/1990 | Buntain et al. | 514/359 |
| 5,232,940 | 8/1993 | Hatton et al. | 514/407 |
| 5,451,598 | 9/1995 | Salmon | 314/404 |
| 5,547,974 | 8/1996 | Hatton et al. | 514/406 |
| 5,580,843 | * 12/1996 | Stetter et al. | 514/341 |
| 5,585,329 | 12/1996 | Royalty et al. | 504/282 |
| 5,608,077 | 3/1997 | Hatton et al. | 548/365.1 |
| 5,629,335 | 5/1997 | Manning et al. | 514/407 |
| 5,637,607 | 6/1997 | Pilato et al. | 514/404 |
| 5,691,333 | 11/1997 | Wu et al. | 514/226.5 |
| 5,696,144 | 12/1997 | Royalty et al. | 514/404 |
| 5,707,934 | 1/1998 | Royalty et al. | 504/253 |
| 5,714,191 | 2/1998 | Hatton et al. | 426/532 |
| 5,716,977 | 2/1998 | Colliot et al. | 514/407 |

FOREIGN PATENT DOCUMENTS

| | | |
|---|---|---|
| 0 295 117 | 12/1988 | (EP) . |
| 0 418 016 | 5/1995 | (EP) . |
| 738713 | * 10/1996 | (EP) . |
| 93/06089 | * 4/1993 | (WO) . |
| 94/29268 | 12/1994 | (WO) . |
| 98/28279 | 7/1998 | (WO) . |

* cited by examiner

Primary Examiner—Laura L. Stockton
(74) Attorney, Agent, or Firm—Joseph C. Gil

(57) ABSTRACT

The invention relates to new 3-thiocarbarnoylpyrazole derivatives of the formula (I)

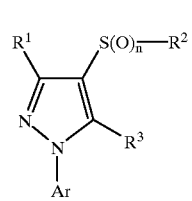

(I)

in which

Ar represents in each case optionally substituted phenyl or pyridyl, $R^1$ represents $H_2N$—CS— and $R^2$ and $R^3$ are as defined in the description, to a plurality of processes for their preparation and to their use as pesticides.

14 Claims, No Drawings

3-THIOCARBAMOYLPYRAZOLE DERIVATIVES AS PESTICIDES

This application is a 371 of PCT/EP97/06503 filed Nov. 21, 1997.

The invention relates to new 3-thiocarbamoylpyrazole derivatives, to a plurality of processes for their preparation, and to their use as pesticides.

It has already been disclosed that certain substituted 1-arylpyrazoles such as, for example, 5-amino-1-[2,6-dichloro-4-(trifluoromethyl)phenyl]-3-cyano-4-[(trifluoromethyl)-sulphinyl]-1H-pyrazole, exhibit a good activity against pests (cf. for example EP-A 295 117 and EP-A 352 944).

Also described are a large number of substituted 1-arylpyrazoles which can be employed for controlling pests (cf., for example, EP-A 201 852, EP-A 418 016 or EP-A 0 659 745).

However, the level of action or duration of action of the prior-art compounds is not entirely satisfactory in all fields of application, in particular in the case of specific insects or when low concentrations are applied.

There have now been found new 3-thiocarbamoylpyrazole derivatives of the general formula (I)

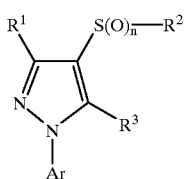

(I)

in which $R^1$ represents $H_2N$—CS—, $R^2$ represents halogenoalkyl, halogenoalkenyl or halogenoalkinyl, $R^3$ represents hydrogen, amino or one of the following groups:

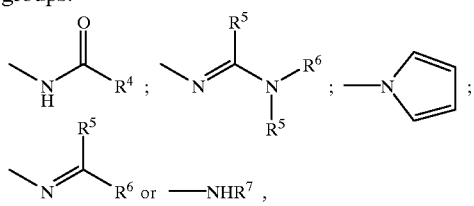

where $R^4$ represents alkyl, halogenoalkyl, alkoxyalkyl or in each case optionally substituted phenyl or pyridyl, $R^5$ represents hydrogen or alkyl, $R^6$ represents hydrogen, alkyl or in each case optionally substituted phenyl or pyridyl and $R^7$ represents alkyl, alkenyl, alkinyl, formyl, alkylcarbonyl, halogenoalkylcarbonyl or alkoxycarbonyl;

Ar represents in each case optionally substituted phenyl or pyridyl and n represents a number 0, 1 or 2.

It has furthermore been found that the new 3-thiocarbamoylpyrazole derivatives of the formula (I) are obtained when a) 3-cyanopyrazole derivatives of the formula (II)

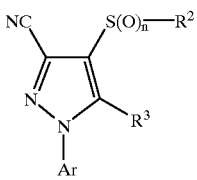

(II)

in which

Ar, $R^2$, $R^3$ and n are as defined above are reacted with hydrogen sulphide, if appropriate in the presence of a reaction auxiliary and if appropriate in the presence of a diluent; or b) 3-thiocarbamoylpyrazole derivatives of the formula (III)

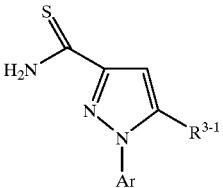

(III)

in which

Ar is as defined above and $R^{3-1}$ represents one of the following groups:

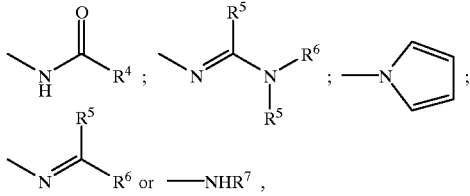

where $R^4$, $R^5$, $R^6$ and $R^7$ are as defined above are reacted with sulphenyl halides of the formula (IV)

Hal—S—$R^2$  (IV)

in which $R^2$ is as defined above and

Hal represents halogen, in particular chlorine or bromine, if appropriate in the presence of a diluent and if appropriate in the presence of a reaction auxiliary; or c) the 2-thiocarbamoylpyrazole derivatives of the formula (Ia)

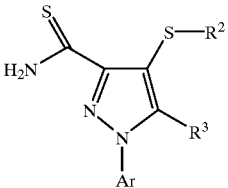

(Ia)

in which

Ar, $R^2$ and $R^3$ are as defined above and which can be obtained by process (a) or (b) are oxidized with oxidants, if appropriate in the presence of a diluent and if appropriate in the presence of a catalyst.

Finally, it has been found that the new 3-thiocarbamoylpyrazole derivatives of the formula (I) have highly pronounced biological properties and are suitable, above all, for controlling animal pests, in particular insects, arachnids and nematodes which occur in agriculture, in forests, in the protection of stored products and materials and in the hygiene sector.

Formula (I) provides a general definition of the compounds according to the invention.

Preferred substituents or ranges of the radicals given in the formulae hereinabove and hereinbelow are illustrated in the following text.

$R^1$ represents $H_2N\text{—}CS\text{—}$.

$R^2$ preferably represents $(C_1\text{–}C_6)$-halogenoalkyl having 1 to 12 halogen atoms; $(C_2\text{–}C_6)$-halogenoalkenyl having 1 to 8 halogen atoms or $(C_2\text{–}C_6)$-halogenoalkinyl having 1 to 6 halogen atoms.

$R^3$ preferably represents hydrogen, amino or one of the following groups:

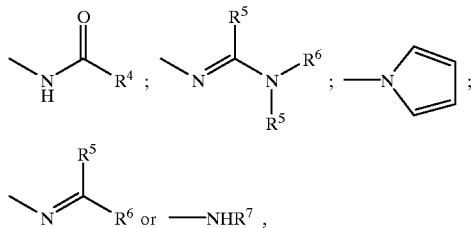

where $R^4$ represents $(C_1\text{–}C_6)$-alkyl, $(C_1\text{–}C_6)$-halogenoalkyl having 1 to 3 halogen atoms, $(C_1\text{–}C_6)$-alkoxy-$(C_1\text{–}C_6)$-alkyl, or represents phenyl or pyridyl, each of which is optionally monosubstituted to trisubstituted by identical or different substituents from the series consisting of cyano, nitro, halogen, $C_1\text{–}C_6$-alkyl, $C_1\text{–}C_6$-alkoxy, $C_1\text{–}C_6$-alkylthio, $C_1\text{–}C_4$-halogenoalkyl, $C_1\text{–}C_4$-halogenoalkoxy or $C_1\text{–}C_4$-halogenoalkylthio having in each case 1 to 5 halogen atoms, $R^5$ represents hydrogen or $(C_1\text{–}C_6)$-alkyl, $R^6$ represents hydrogen, $(C_1\text{–}C_6)$-alkyl, phenyl which is optionally monosubstituted to trisubstituted by identical or different substituents from the series consisting of cyano, nitro, halogen, $C_1\text{–}C_6$-alkyl, $C_1\text{–}C_6$-alkoxy, $C_1\text{–}C_6$-alkylthio, $C_1\text{–}C_4$-halogenoalkyl, $C_1\text{–}C_4$-halogenoalkoxy or $C_1\text{–}C_4$-halogenoalkylthio having in each case 1 to 5 halogen atoms or hydroxyl, or represents pyridyl which is substituted by cyano, nitro, halogen, $C_1\text{–}C_6$-alkyl, $C_1\text{–}C_6$-alkoxy, $C_1\text{–}C_6$-alkylthio, $C_1\text{–}C_4$-halogenoalkyl, $C_1\text{–}C_4$-halogenoalkoxy or $C_1\text{–}C_4$-halogenoalkylthio having in each case 1 to 5 halogen atoms, and $R^7$ represents $(C_1\text{–}C_6)$-alkyl, $(C_2\text{–}C_6)$-alkenyl, $(C_2\text{–}C_6)$-alkinyl, formyl, $(C_1\text{–}C_6)$-alkylcarbonyl, $(C_1\text{–}C_6)$-halogenoalkylcarbonyl having 1 to 6 halogen atoms or $(C_1\text{–}C_6)$-alkoxycarbonyl.

Ar preferably represents phenyl or pyridyl, each of which is optionally monosubstituted to trisubstituted by identical or different substituents from the series consisting of halogen halogeno$(C_1\text{–}C_6)$alkyl, halogeno$(C_1\text{–}C_6)$alkylthio, halogeno$(C_1\text{–}C_6)$alkoxy, $(C_1\text{–}C_6)$alkoxy, methoxy, hydrazino, $(C_1\text{–}C_6)$-dialkylhydrazino, amino, $(C_1\text{–}C_6)$alkylamino, di$(C_1\text{–}C_6)$alkylamino, $(C_1\text{–}C_6)$alkylimino, cyano, $(C_1\text{–}C_6)$alkylthio or the group

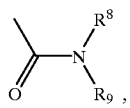

in which $R^8$ and $R^9$ are identical or different and represent hydrogen or $(C_1\text{–}C_6)$-alkyl n preferably represents a number 0, 1 or 2.

$R^1$ represents $H_2N\text{—}CS\text{—}$.

$R^2$ particularly preferably represents $(C_1\text{–}C_4)$-halogenoalkyl having 1 or 9 identical or different halogen atoms from the series consisting of fluorine, chlorine and bromine, $(C_2\text{–}C_4)$-halogenoalkenyl having 1 to 5 identical or different halogen atoms from the series consisting of fluorine, chlorine or bromine or $(C_2\text{–}C_4)$-halogenoalkinyl having 1 to 5 identical or different halogen atoms from the series consisting of fluorine, chlorine and bromine.

$R^3$ especially preferably represents hydrogen, amino or one of the following groups:

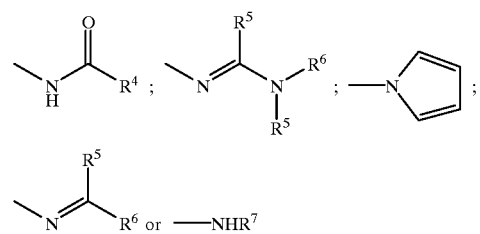

where $R^4$ represents $(C_1\text{–}C_4)$-alkyl, $(C_1\text{–}C_4)$-halogenoalkyl having 1–3 halogen atoms, $(C_1\text{–}C_4)$-alkoxy-$(C_1\text{–}C_2)$-alkyl, or phenyl which is optionally monosubstituted to trisubstituted by identical or different substituents from the series consisting of hydroxyl, cyano, nitro, halogen, $C_1\text{–}C_4$-alkyl, $C_1\text{–}C_4$-alkoxy, $C_1\text{–}C_2$-halogenoalkyl, $C_1\text{–}C_2$-halogenoalkoxy or $C_1\text{–}C_2$-halogenoalkylthio having in each case 1 to 3 halogen atoms, $R^5$ represents hydrogen or $(C_1\text{–}C_4)$-alkyl, $R^6$ represents hydrogen, $(C_1\text{–}C_4)$-alkyl or, or phenyl which is optionally monosubstituted or disubstituted by identical or different substituents from the series consisting of hydroxyl, cyano, nitro, halogen, $C_1\text{–}C_4$-alkyl, $C_1\text{–}C_4$-alkoxy, $C_1\text{–}C_2$-halogenoalkyl, $C_1\text{–}C_2$-halogenoalkoxy or $C_1\text{–}C_2$-halogenoalkylthio having in each case 1 to 3 halogen atoms, in particular 4-hydroxy-3-methoxy-phenyl, and $R^7$ represents $(C_1\text{–}C_4)$-alkyl, $(C_2\text{–}C_4)$-alkenyl, $(C_2\text{–}C_4)$-alkinyl, formyl, $(C_1\text{–}C_4)$-alkylcarbonyl, $(C_1\text{–}C_4)$-halogenoalkylcarbonyl having 1 to 5 identical or different halogen atoms from the series consisting of fluorine, chlorine or bromine or $(C_1\text{–}C_4)$-alkoxycarbonyl.

Ar especially preferably represents phenyl or pyridyl, each of which is optionally monosubstituted to trisubstituted by identical or different substituents from the series consisting of fluorine, chlorine, trifluoromethyl, trifluoromethylthio, trifluoromethoxy, methoxy, hydrazino, dimethylhydrazino, amino, methylamino, dimethylamino, iminomethyl, cyano, methylthio or the group

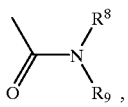

where
R$^8$ and R$^9$ are identical or different and represent hydrogen or (C$_1$–C$_4$)-alkyl.

n especially preferably represents a number 0, 1 or 2.

R$^1$ represents H$_2$N—CS—.

R$^2$ most preferably represents one of the radicals:
—CF$_3$, —CHF$_2$
—CF$_2$—CH$_3$, —CF$_3$—CHF$_2$, —CF$_2$—CHFCl,
—CH$_2$—CF$_3$, —CH$_2$—CF$_2$Cl,
—CH$_2$—CF$_2$—CHF$_2$,
—CF$_2$—CFCl—CF$_3$,
—C(Cl)(CF$_3$)—CF$_2$Cl, —C(Cl)(CF$_3$)—CHCl—CF$_3$,
—C(CF3)=CCl$_2$ R$^3$ most preferably represents hydrogen, amino or one of the groups:
—NH—CO—CH$_3$, —NH—CO—C$_2$H$_5$,
—N=CH—NH$_2$, —N=C(CH$_3$)—NH$_2$,
—N=CH—N(CH$_3$)$_2$, —N=C(CH$_3$)—N(CH$_3$)$_2$,

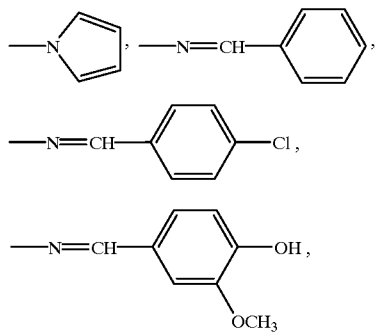

—NHC$_2$H$_5$ or —NH—CH$_2$—CH=CH$_2$.

Ar most preferably represents
(1) phenyl which is disubstituted or trisubstituted by identical or different substituents, where fluorine or chlorine occupies the 2-position, trifluoromethyl the 4-position and fluorine, chlorine, cyano, methoxy, methylthio, trifluoromethyl, trifluoromethoxy, trifluoromethylthio or hydrazino the 6-position; or
(2) a 2-pyridyl radical which is substituted in the 4-position by trifluoromethyl and in the 6-position by fluorine or chlorine.

n most preferably represents one of the integers 0, 1 or 2.

The definitions of radicals or explanations given above or in preferred ranges apply to the end products and analogously to the starting materials and intermediates. These definitions of radicals may be combined with each other as desired, that is to say combinations between the individual preferred ranges, are also possible.

Preferred according to the invention are those compounds of the formula (I) in which there exists a combination of the meanings which have been mentioned above as being preferred (preferable meanings).

Especially preferred according to the invention are those compounds of the formula (I) in which there exists a combination of the meanings mentioned above as especially preferred.

Most preferred according to the invention are those compounds of the formula (I) in which there exists a combination of the meanings mentioned above as most preferred.

In the definitions of radicals given hereinabove and hereinbelow, hydrocarbon radicals such as alkyl or alkenyl—also in compounds containing heteroatoms such as alkoxy or alylthio—are in each case straight-chain or branched, as far as this is possible.

Preferred compounds are those of the formula (1A)

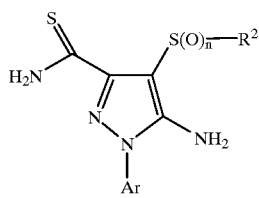

(IA)

in which

Ar, R$^2$ and n are as defined above.

Examples of the new 3-thiocarbamoylpyrazole derivatives are given in Tables 1 to 60:

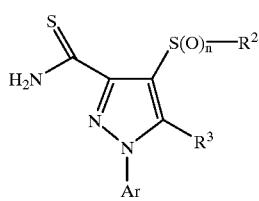

(IB)

Compounds of Table 1 correspond to the general formula (IB) in which

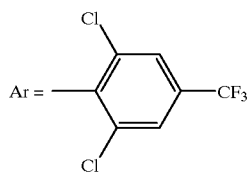

R$^3$=NH$_2$
n=the number 0
R$^2$=as listed below:

TABLE 2

| R$^2$ |
| --- |
| —CF$_3$ |
| —CF$_2$—CH$_3$ |
| —CF$_3$—CHF$_2$ |
| —CF$_2$—CHFCl |
| —CH$_2$—CF$_3$ |
| —CH$_2$—CF$_2$Cl |
| —CH$_2$—CF$_2$—CHF$_2$ |
| —CF$_2$—CFCl—CF$_3$, |
| —C(Cl)(CF$_3$)—CF$_2$Cl |
| —C(Cl)(CF$_3$)—CHCl—CF$_3$ |
| —C(CF$_3$)=CCl$_2$ |

Table 2 contains compounds of the general formula (IB) in which

Ar = 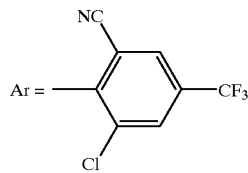

$R^2$, $R^3$ and n=as listed in Table 1.

Table 3

Table 3 contains compounds of the general formula (IB), in which

Ar = 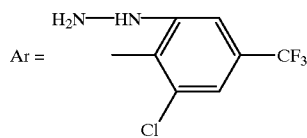

$R^2$, $R^3$ and n=as listed in Table 1.

Table 4

Table 4 contains compounds of the general formula (IB), in which

Ar = 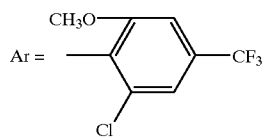

$R^2$, $R^3$ and n=as listed in Table 1.

Tables 5 to 8

Tables 5 to 8 contain compounds of the general formula (IB), in which $R^3$=H

Ar, $R^2$ and n=as listed in Tables 1 to 4.

Tables 9 to 12

Tables 9 to 12 contain compounds of the general formula (IB), in which $R^3$ = 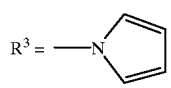

Ar, $R^2$ and n=as listed in Tables 1 to 4.

Tables 13 to 16

Tables 13 to 16 contain compounds of the general formula (IB), in which $R^3$ = 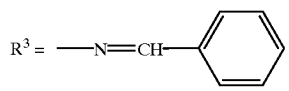

Ar, $R^2$ and n=as listed in Tables 1 to 4.

Tables 17 to 20

Tables 17 to 20 contain compounds of the general formula (IB), in which $R^3$ = 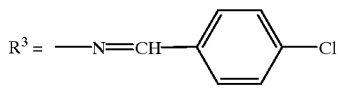

Ar, $R^2$ and n=as listed in Tables 1 to 4.

Tables 21 to 40

Tables 21 to 40 contain compounds of the general formula (IB), in which n=the number 1

Ar, $R^2$ and $R^3$=as listed in Tables 1 to 20.

Tables 41 to 60

Tables 41 to 60 contain compounds of the general formula (IB), in which n=the number 2

Ar, $R^2$ and $R^3$=as listed in Tables 1 to 20.

If, for example, 5-amino-3-cyano-4-(1,1-difluoroethylthio)-1-(2,6-dichloro-4-trifluoromethylphenyl) pyrazole and hydrogen sulphide are used as starting materials, the course of the reaction of process (a) according to the invention can be represented by the following equation:

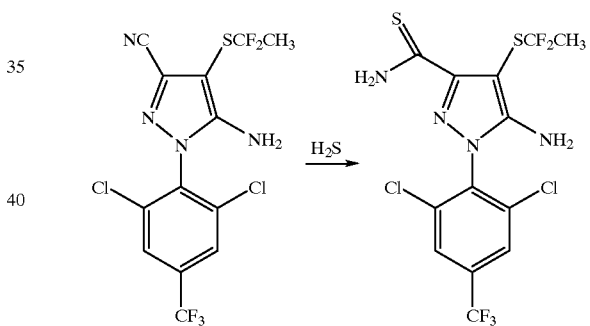

If, for example, 1-(2,6-dichloro-4-trifluoromethylphenyl)-3-thiocarbamoyl-5-(pyrrol-1-yl) pyrazole and 1,1-difluoroethylsulphenyl chloride are used as starting materials, the course of the reaction of process (b) according to the invention can be represented by the following equation:

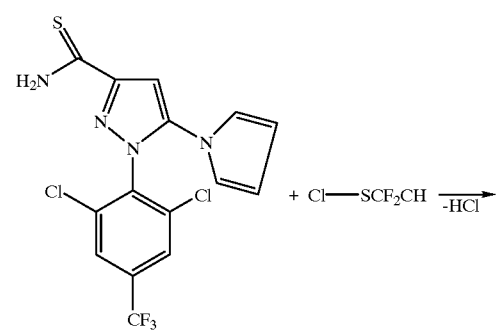

-continued

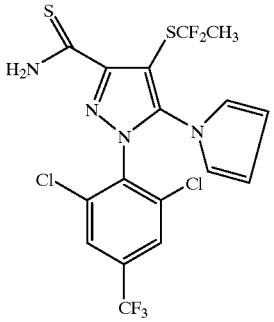

If, for example, 5-(pyrrol-1-yl)-3-thiocarbamoyl-4-(1,1-difluoroethylthio)-1-(2,6-dichloro-4-trifluoromethylphenyl)pyrazole and hydrogen sulphide are used as starting materials, the course of the reaction of process (c) can be represented by the following equation:

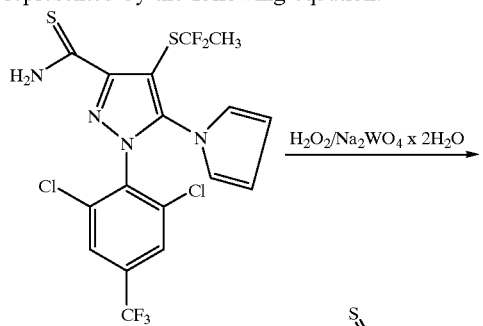

The 3-cyanopyrazole derivatives of the formula (II), which are to be used as starting materials for carrying out process (a) according to the invention, have been disclosed (cf., for example, EP-A 0 295 117 and EP-A 0 659 745) and/or can be prepared analogously to known processes.

The 3-thiocarbamoylpyrazole derivatives of the formula (III), which are to be used as starting materials for carrying out process (b) according to the invention, are new and also an object of the invention.

The compounds of the formula (III) can be obtained by reacting 2-cyanopyrazoles of the formula (V)

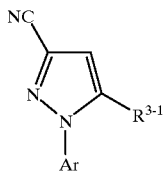

(V)

in which
Ar and $R^{3-1}$ are as defined above with hydrogen sulphide in accordance with process (a) according to the invention, if appropriate in the presence of a reaction auxiliary and if appropriate in the presence of a diluent.

The 3-cyanopyrazoles of the formula (V) are known and/or can be obtained in a known manner, for example by derivatizing the corresponding 5-amino-3-cyanopyrazoles of the formula (VI)

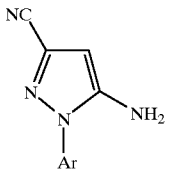

(VI)

in which
Ar is as defined above on the amino group in the customary manner (cf., for example, EP-A 0 659 745).

Alternatively, the compounds of the formula (III) can be obtained by derivatizing 5-amino-3-thiocarbamoylpyrazoles of the formula (VII)

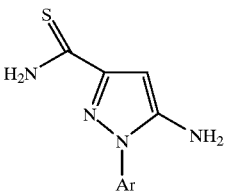

(VII)

in which
Ar is as defined above on the amino group in the customary manner (cf., for example, EP-A 0 659 745).

The 5-amino-3-thiocarbamoylpyrazoles of the formula (VII) are new and also an object of the invention.

They are obtained by reacting 5-amino-3-cyanopyrazoles of the formula (VI) with hydrogen sulphide in accordance with process (a) according to the invention, if appropriate in the presence of a diluent (cf. also the preparation examples).

The sulphenyl halides of the formula (IV), which are also to be used as starting materials in process (b) according to the invention, are generally known compounds of organic chemistry.

The 3-thiocarbamoylpyrazole derivatives of the formula (Ia) which are to be used as starting materials for process (c) according to the invention are compounds according to the invention.

Process (a) according to the invention is preferably carried out using a diluent. Suitable diluents are virtually all inert organic solvents. These include, preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone or methyl isobutyl ketone, esters such as methyl acetate or ethyl acetate, nitriles such as, for example, acetonitrile or propionitrile, amides such as, for example, dimethylformamide, dimethylacetamide and N-methylpyrrolidone, and also dimethyl sulphoxide, tetramethylene sulphone or hexamethylenephosphoric triamide.

Reaction auxiliaries which may be used in process (a) are all bases which can conventionally be used for reactions of this type. The following are preferably suitable: basic nitrogen compounds such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethylaniline, pyridine, 2-methyl-, 3-methyl-, 4-methyl-, 2,4-dimethyl-, 2,6-dimethyl-, 2-ethyl-, 4-ethyl- and 5-ethyl-2-methylpyridine, 1,5-diaza bicyclo[4,3,0]-non-5-ene (DBN), 1,8-diazabicyclo[5,4,0]undec-7-ene (DBU) or 1,4-diazabicyclo-[2,2,2]octane (DABCO). It is also possible to use an excess of reaction auxiliary as the diluent.

When carrying out process (a) according to the invention, the reaction temperatures can be varied within a substantial range. In general, the process is carried out at temperatures between 0° C. and 100° C., preferably at temperatures between 10° C. and 80° C.

Process (a) according to the invention is generally carried out under atmospheric pressure. However, it is also possible to carry out the process under elevated or reduced pressure.

To carry out process (a) according to the invention, an excess of hydrogen sulphide is usually employed. In general, the reactions are carried out in a suitable diluent in the presence of a basic nitrogen compound. Work-up is carried out by customary methods (cf. the preparation examples).

Suitable diluents for carrying out process (b) according to the invention are inert organic solvents. These include, in particular, aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride; ethers such as diethyl ether, dioxane, tetrahydrofuran or ethylene glycol dimethyl ether or ethylene glycol diethyl ether, ketones such as acetone or butanone, nitrites such as acetonitrile or propionitrile; amides such as dimethylformamide, dimethylacetamide, N-methylformanilide, N-methylpyrrolidone or hexamethylphosphoric triamide, esters such as ethyl acetate, sulphoxides such as dimethyl sulphoxide, or acids such as, for example, acetic acid.

If appropriate, process (b) according to the invention can be carried out in the presence of a reaction auxiliary. Suitable reaction auxiliaries are all customary inorganic or organic bases. These include, for example, alkali metal hydroxides such as sodium hydroxide or potassium hydroxide, alkali metal carbonates or hydrogen carbonates such as sodium carbonate, potassium carbonate or sodium hydrogen carbonate, and tertiary amines such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (b) according to the invention, the reaction temperatures may be varied within a wide range. In general, the process is carried out at temperatures between −20° C. and +120° C., preferably at temperatures between 0° C. and +50° C.

To carry out process (b) according to the invention, 1.0 to 2.5 mol, preferably 1.0 to 1.5 mol, of sulphenyl halide of the formula (IV) and, if appropriate, 1.0 to 2.5 mol, preferably 1.0 to 1.5 mol, of reaction auxiliary are generally employed per mol of 1-arylpyrazole which is substituted in the 4-position, of the formula (III). The reaction is carried out and the reaction products are worked up and isolated by generally customary processes.

Suitable oxidants for carrying out process (c) according to the invention are all conventional oxidants which can be used for sulphur oxidation. Especially suitable are hydrogen peroxide, organic peracids such as, for example, peracetic acid, m-chloroperbenzoic acid, p-nitroperbenzoic acid or atmospheric oxygen.

Diluents which are suitable for carrying out process (c) according to the invention are, again, inert organic solvents. The following are preferably used: hydrocarbons such as benzine, benzene, toluene, hexane or petroleum ether; chlorinated hydrocarbons such as dichloromethane, 1,2-dichloroethane, chloroform, carbon tetrachloride or chlorobenzene; ethers such as diethyl ether, dioxane or tetrahydrofuran; carboxylic acids such as acetic acid or propionic acid, or dipolar aprotic solvents such as acetonitrile, acetone, ethyl acetate or dimethylfornamide.

If appropriate, process (c) according to the invention can be carried out in the presence of an acid binder. Suitable acid binders are all organic and inorganic acid binders which can normally be used. The following are preferably used: alkaline earth metal hydroxides, alkaline earth metal acetates, alkaline earth metal carbonates, alkali metal hydroxides, alkali metal acetates or alkali metal carbonates, such as, for example, calcium hydroxcide, sodium hydroxide, sodium acetate or sodium carbonate.

If appropriate, process (c) according to the invention can be carried out in the presence of a suitable catalyst. Suitable catalysts are all those which can normally be used for such sulphur oxidations. Examples which may be mentioned are ammonium molybdate and sodium tungstate.

When carrying out process (c) according to the invention, the reaction temperatures can be varied within a substantial range. In general, the process is carried out at temperatures between −20° C. and +70° C., preferably at temperatures between 0° C. and +50° C.

To carry out process (c) according to the invention, 0.8 to 1.2 mols, preferably equimolar amounts, of oxidant are generally employed per mol of compound of the formula (1a) if oxidation of the sulphur is to be interrupted at the sulphoxide level. For oxidization to the sulphone, 1.8 to 3.0 mols, preferably twice the molar amounts, of oxidant are generally employed per mol of compound of the formula (Ia). The reaction is carried out and the end products are worked up and isolated by customary processes.

The active compounds are well tolerated by plants, show advantageous toxicity to warm-blooded species and are thus suitable for controlling animal pests, in particular insects, arachnids and nematodes, which occur in agriculture, in forests, in the protection of stored products and of materials, and in the hygiene sector. They can preferably be used as crop protection agents. They are active against normally sensitive and resistant species and against all or individual development stages. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp. From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Euryga-ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The plant-parasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp. and Trichodorus spp.

The compounds of the formula (I) according to the invention are distinguished, in particular, by a potent insecticidal activity combined, in some cases, with root-systemic properties.

They can be employed particularly successfully for controlling plant-damaging insects such as, for example, against the mustard beetle larvae (*Phaedon cochlaeriae*), the caterpillars of the diamond-back moth (*Plutella maculipennis*), the green rice leafhopper (*Nephotettix cinctriceps*), the caterpillars of the fall armyworm (*Spodoptera frugiperda*), the peach aphids (*Mycus persicae*) or the larvae of the banded cucumber beetle (*Diabrotica bateata*).

The active compounds can be converted into the customary formulations such as solutions, emulsions, wettable powders, suspensions, powders, dusts, pastes, soluble powders, granules, suspoemulsion concentrates, natural and synthetic products impregnated with active compound, and microencapsulations in polymeric substances.

These formulations are prepared in the known manner, for example by mixing the active compounds with extenders, that is to say liquid solvents and/or solid carriers, if appropriate using surfactants, that is to say emulsifiers and/or dispersants and/or foam formers.

If water is used as extender, it is also possible, for example, to use organic solvents as auxiliary solvents. Suitable liquid solvents are essentially: aromatics such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane, or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite, dolomite, and synthetic granules of inorganic or organic meals and granules of organic material such as sawdust, coconut shells, maize cobs and tobacco stalks; suitable emulsifiers and/or foam formers are: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxymethylcellulose, natural and synthetic polymers in the form of powders, granules or lattices such as gum arabic, polyvinyl alcohol, polyvinyl acetate, and natural phospholipids such as cephalins and lecithins and synthetic phospholipids may be used in the formulations. Other additives may be mineral and vegetable oils.

Colorants such as inorganic pigments, for example iron oxide, titanium oxide, Prussian Blue, and organic dyestuffs such as alizarin, azo and metal phthalocyanin dyes and micronutrients such as salts of iron, manganese, boron, copper, cobalt, molybdenum and zinc may be used.

In general, the formulations comprise between 0.1 and 95% by weight of active compound, preferably between 0.5 and 90%.

In its commercially available formulations and in the use forms prepared with these formulations, the active compound according to the invention may be present in a mixture with other active compounds such as insecticides, attractants, sterilants, bactericides, acaridices, nematicides, fungicides, growth regulators or herbicides. The insecticides include, for example, phosphoric esters, carbamates, carboxylic esters, chlorinated hydrocarbons, phenylureas, substances produced by microorganisms, and the like.

Examples of particularly advantageous components in mixtures are the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thizole-5-carboxanilide; 2,6-dichloroN-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl }-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamates, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflurnizole, triforine, triticonazole, validamycin A, vinclozolin, zineb, ziram Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators is also possible.

Furthermore, the active compounds according to the invention in their commercially available formulations and in the use forms prepared with these formulations, may be present in a mixture with synergists. Synergists are compounds by which the activity of the active compounds is increased without it being necessary for the synergist added to be active itself.

The active compound content of the use forms prepared with the commercially available formulations can vary within wide limits. The active compound concentration of the use forms may range from 0.0000001 to 95% by weight of active compound, preferably between 0.0001 and 1% by weight.

They are applied in a customary manner adapted to suit the use forms.

When used against hygiene and stored-product pests, the active compound is distinguished by an outstanding residual action on wood and clay and by good stability to alkali on limed substrates.

The active compounds according to the invention are not only active against plant, hygiene and stored-product pests, but, in the veterinary medicine sector, also against animal parasites (ectoparasites) such as hard ticks, soft ticks, mange mites, chiggers, flies (stinging and licking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the suborders Amblycerina and Ischnocerina, for example, Trimenopon spp., Menopon spp., Trinoton spp., Bovicola spp., Wemeckiella spp., Lepikentron spp., Damalina spp., Trichodectes spp., Felicola spp.

From the order Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp., Melophagus spp.

From the order of the Siphonapterida, for example, Pulex spp., Ctenocephalides spp., Xenopsylla spp., Ceratophyllus spp.

From the order of the Heteropterida, for example, Cimex spp., Triatoma spp., Rhodnius spp., Panstrongylus spp.

From the order of the Blattarida, for example, *Blatta orientalis, Periplaneta americana, Blattela germanica*, Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp., Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.

For example, they show a good activity against flies (*Musca domestica*), a development-inhibitory action against fly larvae of Lucilla cuprina and a good activity against cockroaches (*Periplaneta americana*) and against ticks (*Boophilus microplus*), also as oviposition inhibitors.

The active compounds of the formula (I) according to the invention are also suitable for controlling arthropods which attack agricultural livestock such as, for example, cattle, sheep, goats, horses, pigs, donkeys, camels, buffaloes, rabbits, chickens, turkeys, ducks, geese, honey bees and other domestic animals such as, for example, dogs, cats, cage birds, aquarium fish and so-called animals for experimentation such as, for example, hamsters, guinea pigs, rats and mice. Controlling these arthropods is intended to reduce deaths and reduced performance (in meat, milk, wool, hides, eggs, honey and the like), so that use of the active compounds according to the invention allows more economical and simpler animal keeping.

In the veterinary sector, the active compounds according to the invention are applied in the known manner by enteral administration in the form of, for example, tablets, capsules, drinks, drenches, granules, pastes, boluses, the feed-through method, suppositories, by parenteral administration, such as, for example, by means of injection (intramuscular, subcutaneous, intravenous, intraperitoneal and the like), implants, by nasal administration, by dermal administration in the form of, for example, dipping or bathing, spraying, pouring-on and spotting-on, washing, dusting, and with the aid of shaped articles containing active compound, such as collars, ear tags, tail tags, limb bands, halters, marking devices and the like.

When used for livestock, poultry, domestic animals and the like, the active compounds of the formula (I) can be applied as formulations (for example powders, emulsions, flowables) which contain the active compounds in an amount of 1 to 80% by weight, either directly or after 100- to 10,000-fold dilution, or as a chemical dip.

Moreover, it has been found that the compounds of the formula (I) according to the invention have a potent insecticidal action against insects which destroy industrial materials.

The following insects may be mentioned by way of example and as being preferred, but without limitation:

Beetles such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*; Xyleborus spec. Tryptodendron spec. *Apate monachus, Bostrychus capucins, Heterobostrychus brunneus*, Sinoxylon spec. *Dinoderus minutus*

Dermapterans such as

*Sirex juvencus, Urocerus gigas, Urocerus gigas taignus, Urocerus augur*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails such as *Lepisma saccarina*.

Technical materials are to be understood as meaning, in the present context, non-live materials such as, preferably, polymers, adhesives, sizes, paper and board, leather, wood and timber products and paints.

Most preferably, the material to be protected from attack from insects is wood and timber products.

Wood and timber products which can be protected by the agent according to the invention or by mixtures comprising this agent are to be understood as meaning, for example: construction timber, wooden beams, railway sleepers, bridge components, jetties, wooden vehicles, boxes, pallets, containers, telephone poles, wooden claddings, windows and doors made from wood, or plywood, chipboard, joiners' work or timber materials which, quite generally, are used in domestic construction or in joinery.

The active compounds can be used as such, in the form of concentrates or generally customary formulations such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellant, if appropriate desiccants and UV stabilizers and, if appropriate, dyes and pigments and other processing auxiliaries.

The insecticides or concentrates employed for the protection of wood and timber products contain the active compound according to the invention in a concentration of 0.0001 to 95% by weight, in particular 0.001 to 60% by weight.

The amount of agents or concentrates employed depends on the species and the abundance of the insects and on the medium. The optimal rate can be determined by test series for each application. In general, however, it will suffice to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent of low volatility or solvent mixture and a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such water-insoluble oily and oil-type solvents of low volatility which are used are suitable mineral oils or their aromatic fractions or mineral-oil-containing solvent mixtures, preferably white spirit, petroleum and/or alkylbenzene.

Mineral oils which are preferably used are those with a boiling range of 170 to 220° C., white spirit with a boiling range of 170 to 220° C., spindle oil with a boiling range of 250 to 350° C., petroleum and aromatics with a boiling range of 160 to 280° C., oil of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene are used, preferably α-monochloronaphthalene.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point above 30° C., preferably above 45° C., and that the insecticide/fungicide mixture is soluble or emulsifiable in this solvent mixture.

In a preferred embodiment, some of the organochemical solvent or solvent mixture is also replaced an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the binding drying oils and/or synthetic resins which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin used as binder can be employed in the form of an emulsion, dispersion or solution. Bitumen or bituminous substances may also be used as binders, in amounts of up to 10% by weight. In addition, colorants, pigments, water repellants, flavour-masking agents and inhibitors or anticorrosive agents and the like, all of which are known per se, can additionally be employed.

The composition or the concentrate preferably comprises, in accordance with the invention, at least one alkyd resin or modified alkyd resin and/or a drying vegetable oil as organochemical binder. Substances which are preferably used in accordance with the invention are alkyd resins with an oil content of over 45% by weight, preferably 50 to 68% by weight.

The abovementioned binder can be replaced fully or in parts by a fixative (mixture) or a plasticizer (mixture). These additives are intended to prevent volatilization of the active compounds, and also crystallization or precipitation. They preferably replace 0.01 to 30% of the binder (based on 100% of the binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl) adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether or ketones such as benzophenone and ethylenebenzophenone.

Another solvent or diluent is, in particular, water, if appropriate in a mixture with one or more of the abovementioned organochemical solvents or diluents, emulsifiers and dispersants.

Particularly effective protection of wood is achieved by industrial-scale impregnating processes, for example vacuum, double-vacuum or pressure processes.

If appropriate, the ready-to-use products may comprise further insecticides and, if appropriate, also one or more fungicides.

Additional components are preferably the insecticides and fungicides mentioned in WO 94/29 268. The compounds mentioned in this document are expressly part of the present invention.

Most preferred components which may be mentioned are insecticides such as chlorpyriphos, phoxim, silafluofin, alphamethrin, cyfluthrin, cypermethrin, delta-methrin, permethrin, imidacloprid, NI-25, flufenoxuron, hexaflumuron and triflumuron, and fungicides such as epoxyconazole, hexaconazole, azaconazole, propiconazole, tebuconazole, cyproconazole, metconazole, imazalil, dichlorfluanid, tolylfluanid, 3-iodo-2-propinyl butylcarbamate, N-octylisothiazolin-3-one and 4,5-dichloro-N-octylisothiazolin-3-one.

Preparation and use of the active compounds according to the invention can be seen from the examples which follow.

Preparation examples

Example 1

11 g (0.024 mol) of 5-amino-3-cyano-4-(1,1-difluoroethylsulphonyl)-1-(2,6-dichloro-4-trifluoromethylphenyl)-pyrazole are dissolved in 80 ml of pyridine and 10 ml of triethylamine. Then, hydrogen sulphide is passed in at room temperature for about 3 hours. The reaction solution is subsequently treated with water and extracted repeatedly with dichloromethane. After drying over magnesium sulphate, the mixture is concentrated by distilling off the solvent in vacuo, and the oily residue is stirred with diethyl ether and filtered off with suction.

This gives 8 g (68% of theory) of 5-amnino-4-(1,1-difluoroethylsulphonyl)-1-(2,6-di chloro-4-trifluoromethylphenyl)-3-thiocarbamoylpyrazole of melting point 228–29° C.

The compounds of the formula (I) shown in Table A below are obtained analogously to Example 1 or in accordance with the general preparation instructions:

TABLE A

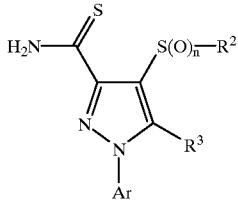

(I)

| Ex. No. | —S(O)$_n$-R$^2$ | R$^3$ | Ar | m.p (° C.) |
|---|---|---|---|---|
| 2 | —S—CF$_2$CH$_3$ | NH$_2$ | 2,6-Cl$_2$-4-CF$_3$-C$_6$H$_2$ | 101 |
| 3 | —S—CH$_2$CF$_2$CF$_3$ | NH$_2$ | 2,6-Cl$_2$-4-CF$_3$-C$_6$H$_2$ | 196 |
| 4 | —SO—CF$_3$ | NH$_2$ | 2,6-Cl$_2$-4-CF$_3$-C$_6$H$_2$ | 203 |
| 5 | —SO—CF$_2$CH$_3$ | NH$_2$ | 2,6-Cl$_2$-4-CF$_3$-C$_6$H$_2$ | 200 |

Preparation of the New Starting Materials of the Formula (VII)

Example (VII-1)

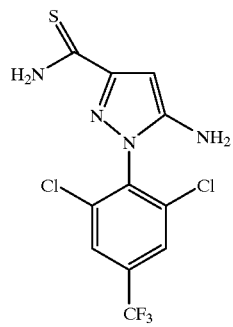

3.8 (0.012 mol) of 5-amino-3-cyano-1-(2,6-dichloro-4-trifluoromethylphenyl)-pyrazole are dissolved in 50 ml of pyridine and 5 ml of triethylamine. Then, hydrogen sulphide is passed in for approx. 2 hours at room temperature, and stirring is subsequently continued for a further 10 minutes at 50° C. The reaction solution is concentrated in vacuo, and the residue which remains is treated with water and dichloromethane. The mixture is extracted repeatedly with dichloromethane and the combined dichloromethane phases are dried over magnesium sulphate and concentrated in vacuo.

This gives 3.4 g (81% of theory) of 5-amino-1-(2,6-dichloro-4-trifluoro methylphenyl)-3-thiocarbamoylpyrazole.

$^1$H-NMR (in DMSO with TMS as the internal standard; δ in ppm): 9.49 (1H); 9.08 (1H); 8.21 (2H); 5.96 (1H); 5.69 (2H).

Preparation of the New Starting Materials of the Formula (III)

Example (III-1)

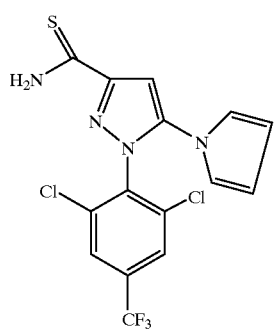

Starting from 3-cyano-1-(2,6-dichloro-4-trifluoromethylphenyl)-5-(pyrrol-1-yl)-pyrazole, Example (III-1) is obtained analogously to Example (VII-1).

$^1$H-NMR (in DMSO with TMS as the internal standard; δ in ppm): 9.95 (1H); 9.58 (1H); 8.30 (2H); 7.19 (1H); 6.20 (2H); 6.13 (2H).

Use Examples

In the use examples which follow, compounds given below are used as comparison substances:

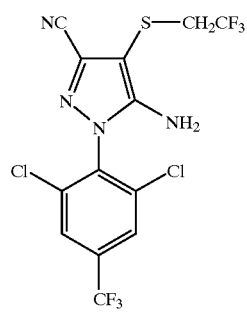
(A)

-continued

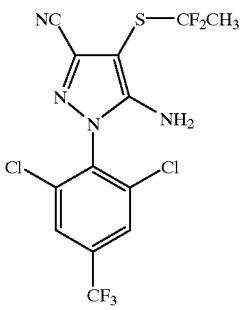
(B)

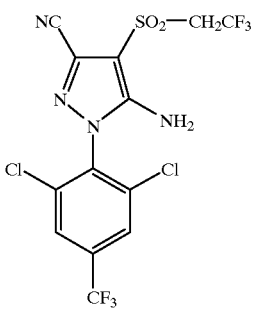
(C)

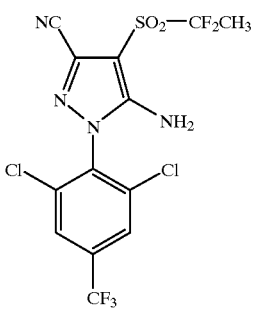
(D)

(All compounds disclosed in EP-A 0 659 745)

Example A

Phaedon Larvae Test

Solvent: 7 parts by weight of dimethylformamide

Emulsifier: 1 part by weight of alkylaryl polyglycol ether

To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with mustard beetle larvae (*Phaedon cochleariae*) while the leaves are still moist.

After the desired time, the destruction rate is determined in %. 100% means that all the beetle larvae have been destroyed; 0% means that none of the beetle larvae have been destroyed.

In this test, an exemplary active compound concentration of 0.00001% of, for example, the compounds of Preparation Examples 1 and 2 caused a destruction rate of 100% after in each case 3 days, while the destruction rate caused by the known compound (A) was only 25%.

Example B
Plutella Test
Solvent: 7 parts by weight of dimethylformamide
Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the diamond-back moth (*Plutella xylostella*) while the leaves are still moist.

After the desired time, the destruction rate is determined in %. 100% means that all the caterpillars have been destroyed; 0% means that none of the caterpillars have been destroyed.

In this test, an exemplary active compound concentration of 0.0001% of, for example, the compound of Preparation Example 1 caused a destruction rate of 75% and of the compound of Preparation Example 2 a destruction rate of 100%, after in each case 3 days, while the known compound (A) showed a destruction rate of only 15%.

Example C
*Spodoptera frugiperda* Test
Solvent: 7 parts by weight of dimethylformamide
Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the fall armyworm (*Spodoptera frugiperda*) while the leaves are still moist.

After the desired time, the destruction rate is determined in %. 100% means that all the caterpillars have been destroyed; 0% means that none of the caterpillars have been destroyed.

In this test, an exemplary active compound concentration of 0.01% of, for example, the compounds of Preparation Examples 1, 2 and 4 caused a destruction rate of 100% after in each case 7 days, while the known compounds (B) and (C) showed a destruction rate of only 10% and no destruction, respectively.

Example D
Nephotettix-test
Solvent: 20 parts by weight of dimethylformamide
Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are populated with green rice leafhoppers (*Nephotettix cincticeps*) while the seedlings are still moist.

After the desired time, the destruction rate is determined in %. 100% means that all the leafhoppers have been destroyed; 0% means that none of the leafhoppers have been destroyed.

In this test, an exemplary active compound concentration of 0.1% of, for example, the compounds of Preparation Examples 2 and 4 caused a destruction rate of 100% and of the compound of Preparation Example 5 a destruction rate of 80% after in each case 6 days, while the known compounds (A) and (D) showed a destruction rate of only 10% and no destruction, respectively.

Example E
Myzus-test
Solvent: 7 parts by weight of dimethylformamide
Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are severely infested with the peach aphid (*Myzus persicae*) are treated by being dipped into the active compound preparation of the desired concentration.

After the desired time, the destruction rate is determined in %. 100% means that all the aphids have been destroyed; 0% means that none of the aphids have been destroyed.

In this test, for example the compounds of the following preparation examples caused the following destruction rates at an exemplary active compound concentration of 0.1%:
1=80%; 2=98% and 4=100%; in each case after 6 days, while the known compound (C) showed an activity of only 50% and the known compound (B) none.

Example F
Limit Concentration Test/soil-dwelling Insects

| Test insect | *Diabrotica balteata* larvae in the soil |
|---|---|
| Solvent | 4 parts by weight of acetone |
| Emulsifier | 1 part by weight of alkylaryl polyglycol ether |

To prepare a suitable preparation of active compound, 1 part by weight of active compound is mixed with the stated amount of solvent, the stated amount of emulsifier is added, and the concentrate is diluted with water to the desired concentration. The concentration of the active compound in the preparation is of virtually no importance, only the amount by weight of active compound per unit volume soil, which is given in ppm (mg/l), being decisive. The soil is filled into 0.5 l pots and the pots are left to stand at 20° C.

Immediately after setting up the test, 5 pregerminated maize kernels are placed into each pot. After 1 day, the test insects are placed into the treated soil. After a further 7 days, the efficacy of the active compound is determined in % by counting the dead and live test insects. The efficacy is 100% when all test insects have been destroyed and 0% when just as many test insects are still alive as in the untreated control.

In this test, for example the compounds of Preparation Examples 2, 4 and 5 caused a destruction rate of 100% at an exemplary active compound concentration of 0.002%.

Example G
Limit Concentration Test/root-systemic Action

| Test insect | *Phaedon cochleariae* larvae |
|---|---|
| Solvent | 4 parts by weight of acetone |
| Emulsifier | 1 part by weight of alkylaryl polyglycol ether |

To prepare a suitable preparation of active compound, 1 part by weight of active compound is mixed with the stated amount of solvent, the stated amount of emulsifier is added, and the concentrate is diluted with water to the desired concentration.

The active compound preparation is mixed intimately with soil. The concentration of the active compound in the preparation is of virtually no importance, only the amount by weight of active compound per unit volume soil, which is given in ppm (=mg/l), being decisive. The treated soil is filled into pots and the pots are planted with cabbage (*Brassica oleracea*). In this manner, the active compound can be taken up from the soil by the roots of the plants and transported into the leaves.

To demonstrate the root-systemic effect, the leaves are populated with the abovementioned test animals after 7 days. After a further 2 days, the test is evaluated by counting or estimating the dead animals. The root-systemic effect of the active compound is deduced from the destruction figures. It is 100% when all the test animals have been destroyed and 0% when just as many test insects are still alive as in the untreated control.

In this test, for example the compounds of Preparation Examples 1, 4 and 5 caused a destruction rate of 100% at an exemplary active compound concentration of 0.002%.

Example H
Fly Test (*Musca domestica*)

| Test animals | Adult *Musca domestica*, strain Reichswald (OP, SP, carbamate-resistant) |
|---|---|
| Solvent | 35 parts by weight of ethylene glycol monomethyl ether 35 parts by weight of nonylphenyl polyglycol ether |

To produce a suitable formulation, three parts by weight of active compound are mixed with seven parts of the abovementioned solvent/emulsifier mixture and the resulting emulsion concentrate is diluted with water to the concentration desired in each case.

2 ml of this active compound preparation are pipetted onto filter paper dishes (φ9.5 cm) which are located in Petri dishes of a suitable size. After the filter discs have been dried, 25 test animals are introduced into the Petri dish and covered.

The efficacy of the active compound preparation is determined after 1, 3, 5 and 24 hours. 100% means that all of the flies have been destroyed; 0% means that none of the flies have been destroyed.

In this test, for example, the compounds of Preparation Examples 1, 2, 4 and 5 showed an activity of 100% at an exemplary active compound concentration of 100 ppm.

Example I
Fly Larvae Test/development-inhibitory Action

| Test animals | All instars of *Lucilia cuprina* (OP-resistant) [pupae and adults (no contact with the active compound)] |
|---|---|
| Solvent | 35 parts by weight of ethylene glycol monomethyl ether 35 parts by weight of nonylphenyl polyglycol ether |

To produce a suitable formulation, three parts by weight of active compound are mixed with seven parts of the abovementioned solvent/emulsifier mixture and the resulting emulsion concentrate is diluted with water to the concentration desired in each case.

For each concentration, 30–50 larvae are transferred onto horse meat (1 cm$^3$) located in glass tubes, and 500 μl of the dilution to be tested are pipetted onto the horse meat. The glass tubes are placed into plastic beakers whose bottoms are covered with sea sand and kept in a controlled-environment cabinet (26° C.±1.5° C., rel. humidity 70%±10%). The action is checked after 24 hours and after 48 hours (larvicidal action). After the larvae have left the glass tubes (approx. 72 hours), the latter are removed, and the beakers are covered with perforated plastic lids. After 1½ times the development time (hatching of control flies), the hatched flies and the pupae/puparia are counted.

The criterion for the effect is death in the case of the treated larvae after 48 hours (larvicidal effect), or the inhibition of the hatching of adults from the pupae, or the inhibition of pupation. The criterion for the in-vitro action of a substance is the inhibition of flea development, or a developmental standstill prior to the adult stage. 100% larvicidal action means that all larvae have died after 48 hours. 100% development-inhibitory action means that no adult flies have hatched.

In this test, for example the compounds according to Preparation Examples 1, 2, 4 and 5 showed an activity of 100% at an exemplary active compound concentration of 100 ppm.

Example J
Test with Resistant *Boophilus microplus*/SP-resistant Parkhurst Strain

| Test animals | Female adults which have sucked themselves full |
|---|---|
| Solvent | 35 parts by weight of ethylene glycol monomethyl ether 35 parts by weight of nonylphenyl polyglycol ether |

To produce a suitable formulation, three parts by weight of active compound are mixed with seven parts of the abovementioned solvent/emulsifier mixture and the resulting emulsion concentrate is diluted with water to the concentration desired in each case.

10 resistant *Boophilus microplus* adults are immersed for 1 minute in the active compound preparation to be tested. After they have been transferred into plastic beakers and kept in a controlled-environment cabinet, the degree of destruction is determined.

100% means that all the ticks have been destroyed; 0% means that none of the ticks have been destroyed.

In this test, for example the compounds of Preparation Examples 2, 4 and 5 showed an activity of 100% at an exemplary active compound concentration of 100 ppm.

Example K
Test with Resistant Boophilus microplus/SP-resistant Parkhurst Strain

| Test animals | Female adults which have sucked themselves full |
|---|---|
| Solvent | Dimethylsulphoxide |

20 mg of the active compound are dissolved in 1 ml of dimethyl sulphoxide, and lesser concentrations are prepared by dilution with the same solvent.

The test is carried out in 5 replications. 1 μl of the solutions is injected into the abdomen and the animals are transferred into dishes and kept in a controlled-environment cabinet. The activity is determined via the inhibition of oviposition. 100% means that none of the ticks has laid eggs.

In this test, the compounds of Preparation Examples 1, 3, 4 and 5 showed an activity of 100% at an exemplary active compound concentration of 20 μg/animal.

Example L
Cockroach Test

| | |
|---|---|
| Test animals | *Periplaneta americana* |
| Solvent | 35 parts by weight of ethylene glycol monomethyl ether |
| | 35 parts by weight of nonylphenyl polyglycol ether |

To produce a suitable formulation, three parts by weight of active compound are mixed with seven parts of the abovementioned solvent/emulsifier mixture and the resulting emulsion concentrate is diluted with water to the concentration desired in each case.

2 ml of this active compound preparation are pipetted onto filter paper discs (φ9.5 cm) located in Petri dishes of a suitable size. After the filtered discs have dried, 5 test animals *Periplaneta americana* are transferred and covered.

After 3 days, the activity of the active compound preparation is determined. 100% means that all the cockroaches have been destroyed; 0% means that none of the cockroaches have been destroyed.

In this test, for example the compounds of Preparation Examples 1 and 2 showed an activity of 100% at an exemplary active compound concentration of 100 ppm.

What is claimed is:

1. A compound of the formula (I)

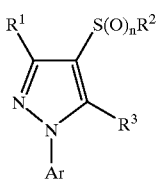

(I)

wherein
$R^1$ represents $H_2N-CS-$,
$R^2$ represents halogenoalkyl, halogenoalkenyl or halogenoalkynyl,
$R^3$ represents amino or a compound selected from the group consisting of

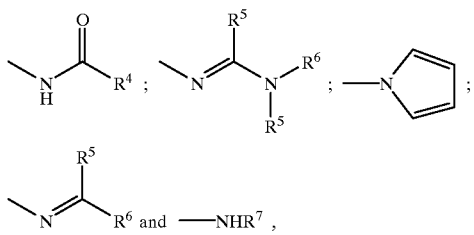

wherein
$R^4$ represents alkyl, halogenoalkyl, alkoxyalkyl or in each case unsubstituted or substituted phenyl or pyridyl,
$R^5$ represents hydrogen or alkyl,
$R^6$ represents hydrogen, alkyl or in each case unsubstituted or substituted phenyl or pyridyl and
$R^7$ represents alkenyl, alkynyl, or halogenoalkylcarbonyl,
Ar represents phenyl or pyridyl, each of which is unsubstituted or monosubstituted to trisubstituted by identical or different substituents selected from the group consisting of halogen, halogeno($C_1$–$C_6$)alkyl, halogeno($C_1$–$C_3$)alkylthio, halogeno($C_1$–$C_6$)alkoxy, ($C_1$–$C_6$)alkoxy, methoxy, hydrazino, ($C_1$–$C_6$)dialkylhydrazino, amino, ($C_1$–$C_6$)alkylimino, di($C_1$–$C_6$)alkylamino, ($C_1$–$C_6$)alkylimino, cyano, ($C_1$–$C_6$)alkylthio and

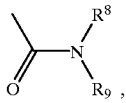

wherein
$R^8$ and $R^9$ are identical or different and represent hydrogen or ($C_1$–$C_6$)alkyl, and
n represents a number 0, 1 or 2.

2. A compound of the formula (III)

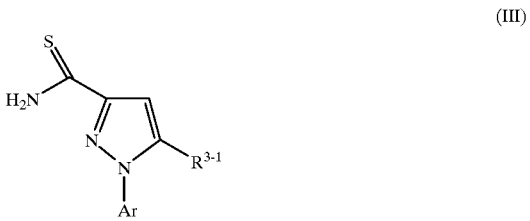

(III)

wherein
Ar represents phenyl or pyridyl, each of which is unsubstituted or monosubstituted to trisubstituted by identical or different substituents selected from the group consisting of halogen, halogeno($C_1$–$C_6$)alkyl, halogeno ($C_1$–$C_3$)alkylthio, halogeno($C_1$–$C_6$)alkoxy, ($C_1$–$C_6$) alkoxy, methoxy, hydrazino, ($C_1$–$C_6$)-dialkylhydrazino, amino, ($C_1$–$C_6$)alkylamino, di($C_1$–$C_6$)alkylamino, ($C_1$–$C_6$)alkylimino, cyano, ($C_1$–$C_6$)alkylthio and

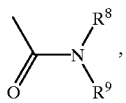

wherein
$R^8$ and $R^9$ are identical or different and represent hydrogen or ($C_1$–$C_6$)alkyl, and
$R^{3-1}$ represents one of the following groups,

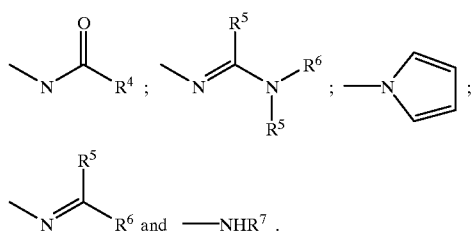

wherein
$R^4$ represents alkyl, halogenoalkyl, alkoxyalkyl or in each case unsubstituted or substituted phenyl or pyridyl,
$R^5$ represents hydrogen or alkyl,
$R^6$ represents hydrogen, alkyl or in each case unsubstituted or substituted phenyl or pyridyl and $R^7$ represents alkenyl, alkynyl, or halogenoalkylcarbonyl.

3. A compound of the formula (VII)

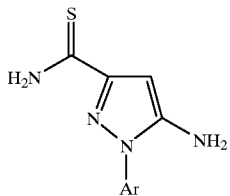

(VII)

wherein

Ar represents phenyl or pyridyl, each of which is unsubstituted or monosubstituted to trisubstituted by identical or different substituents selected from the group consisting of halogen, halogeno($C_1$–$C_6$)alkyl, halogeno($C_1$–$C_3$)alkylthio, halogeno($C_1$–$C_6$)alkoxy, ($C_1$–$C_6$)alkoxy, methoxy, hydrazino, ($C_1$–$C_6$)-dialkylhydrazino, amino, ($C_1$–$C_6$)alkylamino, di($C_1$–$C_6$)alkylamino, ($C_1$–$C_6$)alkylimino, cyano, ($C_1$–$C_6$)alkylthio and

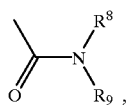

wherein $R^8$ and $R^9$ are identical or different and represent hydrogen or ($C_1$–$C_6$)alkyl.

4. A compound according to claim 1 wherein $R^2$ represents ($C_1$–$C_6$)-halogenoalkyl having 1 to 12 halogen atoms, ($C_2$–$C_6$)-halogenoalkenyl having 1 to 8 halogen atoms or ($C_2$–$C_6$)-halogenoalkynyl having 1 to 6 halogen atoms, $R^3$ represents amino or a compound selected from the group consisting of

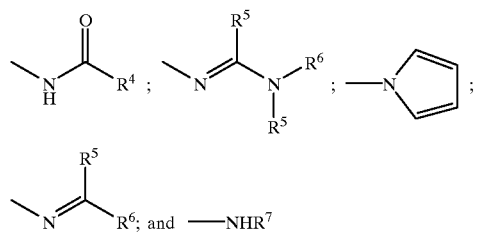

wherein $R^4$ represents ($C_1$–$C_6$)-alkyl, ($C_1$–$C_6$)-halogenoalkyl having 1 to 3 halogen atoms, ($C_1$–$C_6$)-alkoxy-($C_1$–$C_6$)-alkyl, or represents phenyl or pyridyl, each of which is unsubstituted or mono-substituted to trisubstituted by identical or different substituents selected from the group consisting of cyano, nitro, halogen, ($C_1$–$C_6$)-alkyl, ($C_1$–$C_6$)-alkoxy, ($C_1$–$C_6$)-alkylthio, ($C_1$–$C_4$)-halogenoalkyl, ($C_1$–$C_4$)-halogenoalkoxy and ($C_1$–$C_4$)-halogenoalkylthio having in each case 1 to 5 halogen atoms, $R^5$ represents hydrogen or ($C_1$–$C_6$)-alkyl, $R^6$ represents hydrogen, ($C_1$–$C_6$)-alkyl, phenyl which is unsubstituted or monosubstituted to trisubstituted by identical or different substituents selected from the group consisting of cyano, nitro, halogen, ($C_1$–$C_6$)-alkyl, ($C_1$–$C_6$)-alkoxy, ($C_1$–$C_6$)-alkylthio, ($C_1$–$C_4$)-halogenoalkyl, ($C_1$–$C_4$)-halogenoalkoxy and ($C_1$–$C_4$)-halogenoalkylthio having in each case 1 to 5 halogen atoms or hydroxyl, or represents pyridyl which is substituted by a compound selected from the group consisting of cyano, nitro, halogen, ($C_1$–$C_6$)-alkyl, ($C_1$–$C_6$)-alkylthio, ($C_1$–$C_4$)-halogenoalkyl, ($C_1$–$C_4$)-halogenoalkoxy and ($C_1$–$C_4$)-halogenoalkylthio having in each case 1 to 5 halogen atoms, and $R^7$ represents ($C_2$–$C_6$)-alkenyl, ($C_2$–$C_6$)-alkynyl, or ($C_1$–$C_6$)-halogenoalkylcarbonyl having 1 to 6 halogen atoms.

5. A compound according to claim 1 wherein $R^2$ represents ($C_1$–$C_4$)-halogenoalkyl having 1 or 9 identical or different halogen atoms selected from the group consisting of fluorine, chlorine and bromine, ($C_2$–$C_4$)-halogenoalkenyl having 1 to 5 identical or different halogen atoms selected from the group consisting of fluorine, chlorine and bromine or ($C_2$–$C_4$)-halogenoalkynyl having 1 to 5 identical or different halogen atoms selected from the group consisting of fluorine, chlorine and bromine, $R^3$ represents amino or a compound selected from the group consisting of

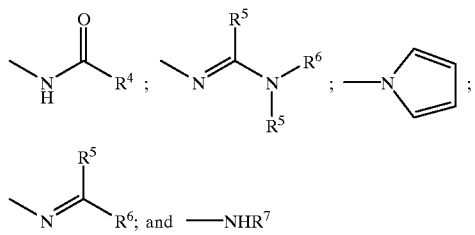

wherein $R^4$ represents ($C_1$–$C_4$)-alkyl, ($C_1$–$C_4$)-halogenoalkyl having 1–3 halogen atoms, ($C_1$–$C_4$)-alkoxy-($C_1$–$C_2$)-alkyl, or phenyl which is unsubstituted or monosubstituted to trisubstituted by identical or different substituents selected from the group consisting of hydroxyl, cyano, nitro, halogen, ($C_1$–$C_4$)-alkyl, ($C_1$–$C_4$)-alkoxy, ($C_1$–$C_2$)-halogenoalkyl, ($C_1$–$C_2$)-halogenoalkoxy and ($C_1$–$C_2$)-halogenoalkylthio having in each case 1 to 3 halogen atoms, $R^5$ represents hydrogen or ($C_1$–$C_4$)-alkyl, $R^6$ represents hydrogen, ($C_1$–$C_4$)-alkyl, or phenyl which is unsubstituted or monosubstituted or disubstituted by identical or different substituents selected from the group consisting of hydroxyl, cyano, nitro, halogen, ($C_1$–$C_4$)-alkyl, ($C_1$–$C_4$)-alkoxy, ($C_1$–$C_2$)-halogenoalkyl, ($C_1$–$C_2$)-halogenoalkoxy and ($C_1$–$C_2$)-halogenoalkylthio having in each case 1 to 3 halogen atoms, or 4-hydroxy-3-methoxy-phenyl, and $R^7$ represents ($C_2$–$C_4$)-alkenyl, ($C_2$–$C_4$)-alkynyl, or ($C_1$–$C_4$)-halogenoalkylcarbonyl having 1 to 5 identical or different halogen atoms selected from the group consisting of fluorine, chlorine and bromine, and Ar represents phenyl or pyridyl, each of which is unsubstituted or mono-substituted to trisubstituted by identical or different substituents selected from the group consisting of fluorine, chlorine, trifluoromethyl, trifluoromethylthio, trifluoromethoxy, methoxy, hydrazino, dimethylhydrazino, amino, methylamino, dimethylamino, iminomethyl, cyano, methylthio and the group

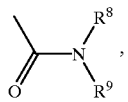

wherein
$R^8$ and $R^9$ are identical or different and represent hydrogen or $(C_1–C_4)$-alkyl.

6. A compound according to claim 1, wherein
$R^2$ represents a compound selected from the group consisting of
—$CF_3$, —$CHF_2$
—$CF_2$—$CH_3$, —$CF_3$—$CHF_2$, —$CF_2$—$CHFCl$,
—$CH_2$—$CF_3$, —$CH_2$—$CF_2Cl$
—$CH_2$—$CF_2$—$CHF_2$,
—$CF_2$—$CFCl$—$CF_3$,
—$C(Cl)(CF_3)$—$CF_2Cl$, —$C(Cl)(CF_3)$—$CHCl$—$CF_3$, and
—$C(CF_3)$=$CCl_2$, $R^3$ represents amino or a compound selected from the group consisting of
—NH—CO—$CH_3$,—NH—CO—$C_2H_5$,
—N=CH—$NH_2$,—N=C($CH_3$)—$NH_2$,
—N=CH—N($CH_3$)$_2$,—N=C($CH_3$)—N($CH_3$)$_2$,

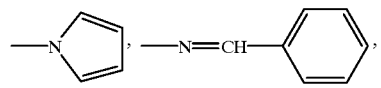

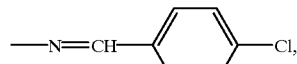

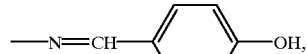

Ar represents phenyl which is disubstituted or trisubstituted by identical or different substituents, where fluorine or chlorine occupies the 2-position, trifluoromethyl the 4-position and fluorine, chlorine, cyano, methoxy, methylthio, trifluoromethyl, trifluoromethoxy, trifluoromethylthio or hydrazine the 6-position.

7. A pesticide, comprising at least one compound of the formula (I) according to claim 1 and one or more extenders and/or surfactants.

8. A method of controlling pests, comprising the step of allowing a compound of the formula (I) according to claim 1 to act on pests and/or their environment.

9. A process for the preparation of a compound of the formula (I) according to claim 1, comprising the step of:
a) reacting a 3-cyanopyrazole derivative of the formula (II)

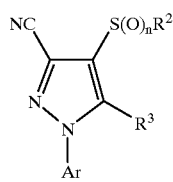

wherein
Ar, $R^2$, $R^3$ and n are as defined in claim 1, with hydrogen sulphide, or b) reacting a 3-thiocarbamoylpyrazole derivative of the formula (III)

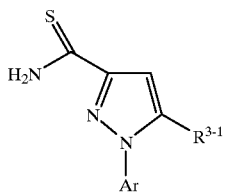

wherein
Ar is as defined in claim 1, and $R^{3-1}$ represents a compound selected from the group consisting

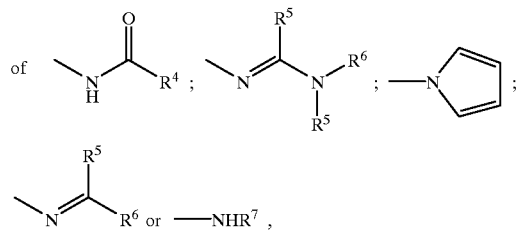

wherein
$R^4$, $R^5$, $R^6$ and $R^7$ are as defined in claim 1, with a sulphenyl halide of the formula (IV)

Hal—S—$R^2$ (IV)

wherein
$R^2$ is as defined in claim 1, and
Hal represents halogen, or c) oxidizing a 2-thiocarbamoylpyrazole derivative of the formula (Ia)

(Ia)

wherein
Ar, $R^2$ and $R^3$ are as defined in claim 1, with an oxidant.

10. The process of claim 9 wherein the reaction is carried out in the presence of a reaction auxiliary.

11. The process of claim 9 wherein the reaction is carried out in the presence of a diluent.

12. The process of claim 9 wherein the reaction is carried out in the presence of a reaction auxiliary and a diluent.

13. A process for the preparation of a pesticide, comprising the step of mixing a compound of the formula (I) according to claim 1 with extenders and/or surfactants.

14. The compound of claim 6 wherein n is 1, $R^2$ represents —$CF_3$, $R^3$ represents amino and Ar represents a trisubstituted phenyl with chlorine in the 2- and 6-position and trifluoromethyl in the 4-position.

* * * * *